United States Patent
Cree et al.

(10) Patent No.: US 10,507,259 B2
(45) Date of Patent: Dec. 17, 2019

(54) FLEXIBLE ABSORBENT PAD

(71) Applicant: First Quality Retail Services, LLC, Great Neck, NY (US)

(72) Inventors: James William Cree, Loveland, OH (US); Jocelyn Rice, Philadelphia, PA (US)

(73) Assignee: FIRST QUALITY RETAIL SERVICES, LLC, Great Neck, NY (US)

( * ) Notice: Subject to any disclaimer, the term of this patent is extended or adjusted under 35 U.S.C. 154(b) by 615 days.

(21) Appl. No.: 15/150,150

(22) Filed: May 9, 2016

(65) Prior Publication Data

US 2016/0324696 A1    Nov. 10, 2016

Related U.S. Application Data

(60) Provisional application No. 62/158,864, filed on May 8, 2015.

(51) Int. Cl.
| | | |
|---|---|---|
| *A61F 13/53* | (2006.01) | |
| *A61F 13/533* | (2006.01) | |
| *A61F 13/539* | (2006.01) | |
| *A61L 15/24* | (2006.01) | |
| *A61L 15/60* | (2006.01) | |

(Continued)

(52) U.S. Cl.
CPC ............ *A61L 15/24* (2013.01); *A61F 13/533* (2013.01); *A61F 13/539* (2013.01); *A61L 15/425* (2013.01); *A61L 15/58* (2013.01); *A61L 15/60* (2013.01); *A61F 2013/530481* (2013.01)

(58) Field of Classification Search
CPC .... A61F 13/532; A61F 13/533; A61F 13/534; A61F 13/53436; A61F 13/535; A61F 13/536; A61F 2013/15292; A61F 2013/153; A61F 2013/15308; A61F 2013/15373;
(Continued)

(56) References Cited

U.S. PATENT DOCUMENTS 3,065,751 A * 11/1962 Gobbo, Sr. ........ A61F 13/15203
                                                          5/487
3,525,337 A *  8/1970 Simons ............ A61F 13/53436
                                                         604/366
(Continued)

FOREIGN PATENT DOCUMENTS

EP       0705583 A1    4/1994
EP       0705586 A1    4/1996
(Continued)

*Primary Examiner* — Catherine L Anderson
(74) *Attorney, Agent, or Firm* — Amster, Rothstein & Ebenstein LLP

(57) ABSTRACT

A flexible absorbent pad has a dry thickness of between 2 mm and 10 mm and a difference in flexural-resistance between the dry state and the wet state of an absorbent center zone of the absorbent pad of less than 100 grams-force. The absorbent core of the pad may include an airlaid, a foam, or a fibrous staple filament. The absorbent core of the absorbent pad may be corrugated, such as with flexure hinges, in which case adhesive is applied to the backsheet of the absorbent pad in a pattern that leaves the flexure hinges devoid of adhesive so that the backsheet is attached to the absorbent core in a manner that does not impede the flexing of the flexure hinges.

17 Claims, 5 Drawing Sheets

(51) Int. Cl.
 *A61L 15/42* (2006.01)
 *A61L 15/58* (2006.01)
(58) Field of Classification Search
 CPC ............ A61F 2013/5326; A61F 13/539; A61F 2013/53908; A61F 2013/53925
 See application file for complete search history.

(56) References Cited

U.S. PATENT DOCUMENTS

| | | | | |
|---|---|---|---|---|
| 3,741,212 | A * | 6/1973 | Schutte | A61F 13/505 |
| | | | | 604/364 |
| 4,578,070 | A * | 3/1986 | Holtman | A61F 13/53436 |
| | | | | 604/372 |
| 4,578,080 | A * | 3/1986 | Helal | A61F 2/30721 |
| | | | | 606/155 |
| 4,950,264 | A | 8/1990 | Osborn, III | |
| 5,383,869 | A | 1/1995 | Osborn, III | |
| 5,550,167 | A | 8/1996 | DesMarais | |
| 5,607,415 | A | 3/1997 | Datta et al. | |
| 5,803,920 | A | 9/1998 | Gilman | |
| 6,500,159 | B1 * | 12/2002 | Carvalho | A61F 13/4704 |
| | | | | 604/358 |
| 6,852,905 | B2 | 2/2005 | Baker | |
| 7,147,628 | B2 * | 12/2006 | Drevik | A61F 13/4755 |
| | | | | 604/385.101 |
| 7,504,553 | B2 * | 3/2009 | Nagahara | A61F 13/15203 |
| | | | | 604/367 |
| 7,753,896 | B2 | 7/2010 | Collado et al. | |
| 8,211,815 | B2 * | 7/2012 | Baker | A61F 13/15707 |
| | | | | 428/179 |
| 9,381,122 | B2 * | 7/2016 | Hashino | A61F 13/539 |
| 2006/0206073 | A1 * | 9/2006 | Crane | A61F 13/5323 |
| | | | | 604/378 |
| 2015/0133883 | A1 | 5/2015 | Cardin et al. | |
| 2015/0238370 | A1 * | 8/2015 | Uda | A61F 13/4756 |
| | | | | 604/370 |

FOREIGN PATENT DOCUMENTS

| | | | |
|---|---|---|---|
| EP | 1088536 | 3/2005 | |
| EP | 1077052 B1 | 4/2005 | |
| JP | 2014-68958 A * | 4/2014 | ........... A61F 13/539 |

* cited by examiner ically relates to flexible absorbent pads, such as a sanitary napkin or an incontinence pad or liner, that contains superabsorbent polymer (SAP) particles.

FLEXIBLE ABSORBENT PAD

FIELD

The present invention generally relates to flexible absorbent pads, such as a sanitary napkin or an incontinence pad or liner, that contains superabsorbent polymer (SAP) particles.

CROSS-REFERENCE TO RELATED APPLICATION

This application claims the benefit of U.S. Provisional Application Ser. No. 62/158,864, filed on May 8, 2015, the entire contents of which are incorporated by reference herein.

BACKGROUND

A conventional superabsorbent pad includes an absorbent laminate that consists mostly of one or two flat tissue layers with superabsorbent powder encapsulated either within the flat tissue layer or sandwiched between the two tissue layers as a laminate core. These pads are advantageously used as hygienic sanitary articles because they can absorb large amounts of liquid, such as urine and menstrual fluid. However, a drawback of most superabsorbent pads is that the laminate core tends to lose flexibility when it absorbs liquid. This loss of flexibility is due to pressure from the wearer and the irreversible deformation of the superabsorbent pad when it becomes wet. Absent some flexibility, the pad becomes uncomfortable to wear. Consequently, a wearer must have a wet absorbent pad changed relatively quickly in order to restore a level of comfort.

SUMMARY

An object of the present invention is to provide a flexible absorbent product, such as a hygienic sanitary article, that is relatively thin and remains flexible and comfortable even after the product absorbs a large amounts of liquid, such as urine and menstrual fluids.

An absorbent pad according to an exemplary embodiment of the present invention comprises multiple layers, including a liquid permeable topsheet (cover), an absorbent core below the topsheet, and a liquid impermeable backsheet having one or more barrier layers below the absorbent core. The absorbent core includes superabsorbent polymer (SAP) particles and extends across at least a portion of the absorbent pad between the topsheet and the backsheet. In at least one embodiment of the present invention, the absorbent difference in flexural resistance between the dry state and the wet state of the absorbent center zone is less than 100 grams-force (gf).

The absorbent core may be formed, for example, from a foam, airlaid or fibrous staple filament, such as carded polyethylene terephthalate (PET) or a mixture of PET and polypropylene (PP) blended through-air or resin bonded fabrics.

In an exemplary embodiment of the present invention, the absorbent pad includes a flexible absorbent core that is corrugated, such as with a plurality of ridges, having a first thickness, that extend lengthwise along the absorbent core interleaved with one or more flexure hinges, of a second thickness less than the first thickness, that also extend lengthwise along the absorbent core. The flexure hinges of the flexible absorbent core allow the absorbent core, which resists flexing in a widthwise direction, to flex along the lengthwise flexure hinges before and after the absorbent core has absorbed liquid and is subject to lateral motion. The flexure hinges also enable the absorbent core to resist deformation from its original shape even when wet. In an embodiment, the absorbent core is a laminate.

In an exemplary embodiment, a bottom of the absorbent core is bonded with a first adhesive to a top of the backsheet that faces the bottom of the absorbent core in the absorbent pad and is applied in a first pattern that enables the absorbent core to remain flexible. Thus, in an embodiment in which the absorbent pad has a corrugated absorbent core, the first adhesive is applied to the plurality of ridges on the bottom of the absorbent core in a first pattern that leaves the flexure hinges substantially devoid of the first adhesive.

In one embodiment, the first adhesive may be applied as the first pattern to each of the plurality of ridges of the absorbent core as a row of droplets. In another embodiment, the first adhesive may be applied as the first pattern to each of the plurality of ridges of the absorbent core as a continuous filament of adhesive connecting a plurality of spaced-apart spirals of adhesive.

In at least one embodiment of the present invention, a second adhesive is applied to a second side of the backsheet to enable the removable attachment of the absorbent pad to a garment, such as consumer underwear. This second adhesive is applied to the second side of the backsheet in a second pattern that enables the absorbent pad to remain flexible. In an embodiment in which in which the absorbent pad has a corrugated absorbent core, the second adhesive is applied to the second side of the backsheet in a second pattern that avoids alignment with the flexure hinges of the absorbent core that face the first side of the backsheet so as not to interfere with the flexure hinges. The second adhesive may be the same as or different from the first adhesive.

In at least one embodiment of the present invention, the absorbent core is located in an absorbent center zone, which is located in the vicinity of the center of the absorbent pad and is resilient. The absorbent center zone is the portion that is intended to be placed by a wearer against the body where bodily fluids may be discharged. In at least one embodiment, the absorbent center zone extends within a range of 20-50% of the absorbent pad.

In at least one embodiment of the present invention, the absorbent pad has a dry thickness of at least 2 mm and no more than 10 mm.

In at least one embodiment of the present invention, the absorbent pad also includes an acquisition distribution layer (ADL) between the topsheet and absorbent core of the absorbent pad.

BRIEF DESCRIPTION OF THE DRAWINGS

Exemplary embodiments of the present invention will be described with references to the accompanying figures, wherein.

DETAILED DESCRIPTION

The present invention generally relates to an absorbent pad that includes a flexible absorbent core, where the absorbent pad is flexible when dry and remains flexible and does not deform even after it absorbs large amounts of liquid.

Figure 1A:
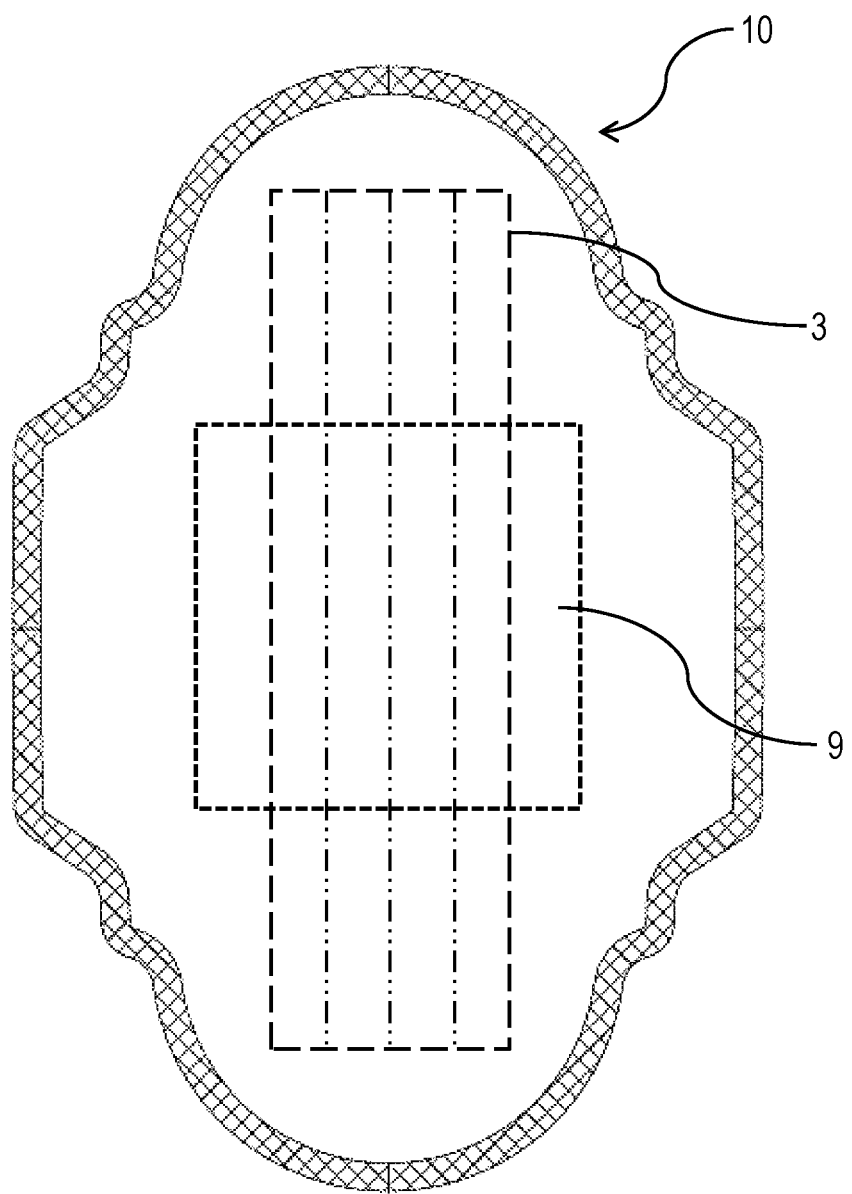
FIG. 1A is a top plan view of an absorbent pad in accordance with an exemplary embodiment of the present invention.
Figure 1B:
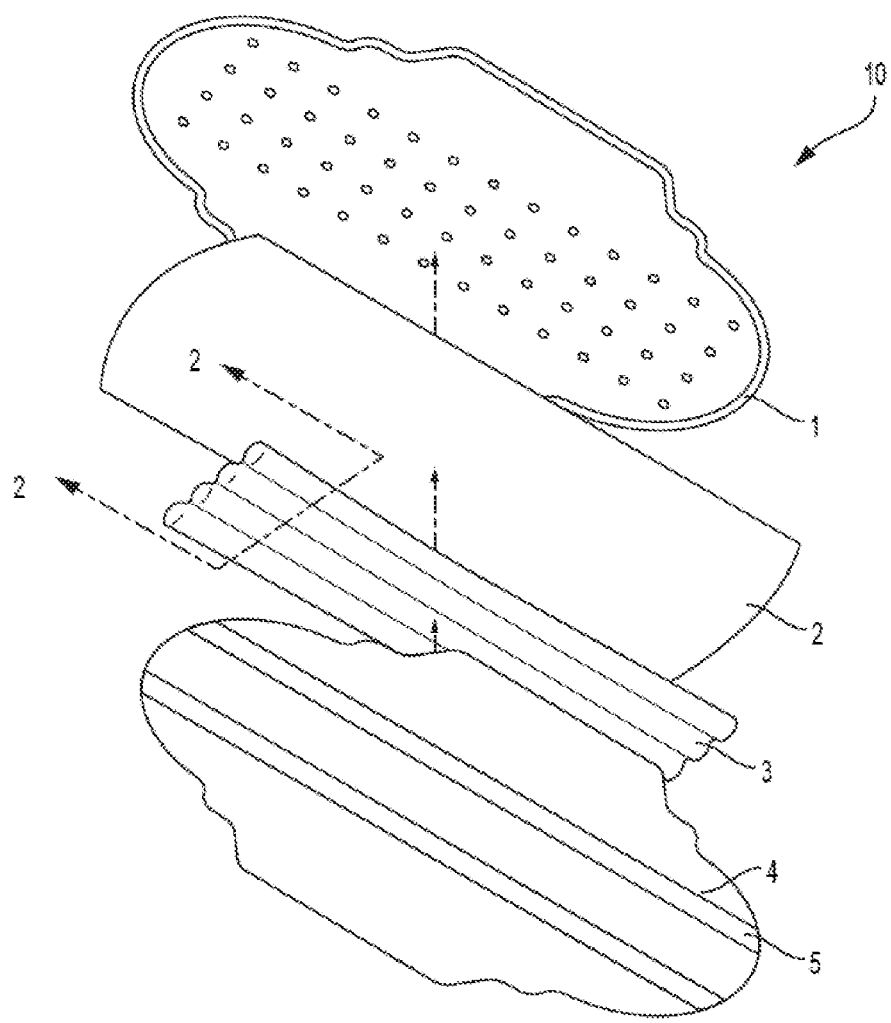
FIG. 1B is an exploded view of the absorbent pad of FIG. 1A from the backsheet upward in accordance with an exemplary embodiment of the present invention.

FIG. 1A shows an absorbent pad, generally designated by reference number 10, according to an exemplary embodiment of the present invention. FIG. 1B shows an exploded view of the absorbent pad 10. Absorbent pad 10 includes the following layers: a liquid permeable topsheet 1 to face a wearer, an optional liquid transfer layer (also known as an acquisition distribution layer) 2 below topsheet 1, an absorbent core 3 with SAP particles below liquid transfer layer 2, and a backsheet 4 comprising one or more barrier layers under absorbent core 3 to face a garment and protect the garment from liquids. Absorbent pad 10 is sealed closed around its border between the topsheet 1 and backsheet 4. Absorbent pad 10 may include optional wings (not shown) on the topsheet and backsheet. Backsheet 4 is generally covered by a removable cover sheet (not shown) when packaged.

In an exemplary embodiment, absorbent core 3 comprises a corrugated laminate with SAP particles that are, for example, trapped within a hydrogen-bonded airlaid material or are sandwiched between a laminate of perforated film and tissue. The SAP particles absorb and retain liquids, such as urine and menstrual fluids, that come into contact with absorbent pad 10 to prevent the liquid from either rewetting the wearer or otherwise leaking out of absorbent pad 10. The laminate can be made, for example, from a foam, airlaid or fibrous staple filament such as carded PET or a mixture of PET and PP blended through-air or resin bonded fabrics. Absorbent pad 10 may be manufactured in a wide variety of sizes and shapes (e.g., rectangular, hourglass, "T"-shaped, asymmetric) and absorbent core 3 may be shaped to conform to the shape of absorbent pad 10 or may be formed in a different shape, such as, for example, as a rectangle, as shown in FIG. 1A. Absorbent core 3 is compressible, conformable to the shape of the wearer's body and does not impede normal movement by the wearer when dry or wet.

Figure 2:
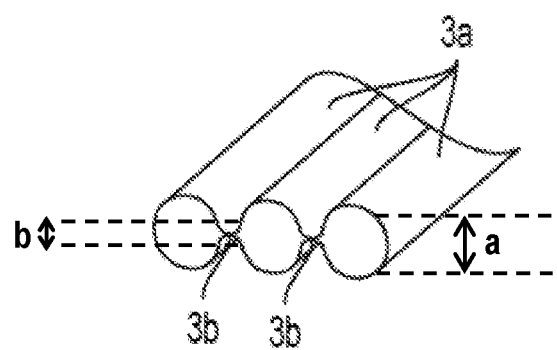
FIG. 2 is a cross-sectional view of the absorbent core along line 2-2 of FIG. 1B.

FIG. 2 shows a cross-section of the exemplary embodiment of absorbent core 3 along line 2-2 of FIG. 1. Absorbent core 3 includes an alternating pattern of ridges 3a and flexure hinges 3b extending in a generally lengthwise direction that enable absorbent core 3 to flex along its length in a widthwise direction. In the illustrated exemplary embodiment, a single flexure hinge 3b separates adjacent ridges 3a to provide the desired flexibility. As used herein, a ridge 3a is a lengthwise section of absorbent core 3 that contains absorbent material, such as SAP particles, and has a first thickness a. In an exemplary embodiment, ridge 3a is round or oval in cross-section. Hinge 3b is a flexure hinge that extends lengthwise between adjacent ridges 3a and has a second thickness b that is less than the first thickness a. For example, first thickness a may be between 1.3 to 1.7 mm and second thickness b may be between 0.5 to 0.9 mm. Flexure hinges 3b enable the ridges 3a to flex relative to one another along the hinge 3b and assist the absorbent pad 10 in maintaining its shape while absorbent pad 10 is under pressure from absorbed liquids. One suitable material that may be used for absorbent core 10 is a Novathin® absorbent core Item No. J2100935DTNBY from EAM Corporation of Jesup, Ga. USA. The spacing between the flexure hinges 3b on the absorbent core may either be fixed or vary across the width of the core.

Figure 3:
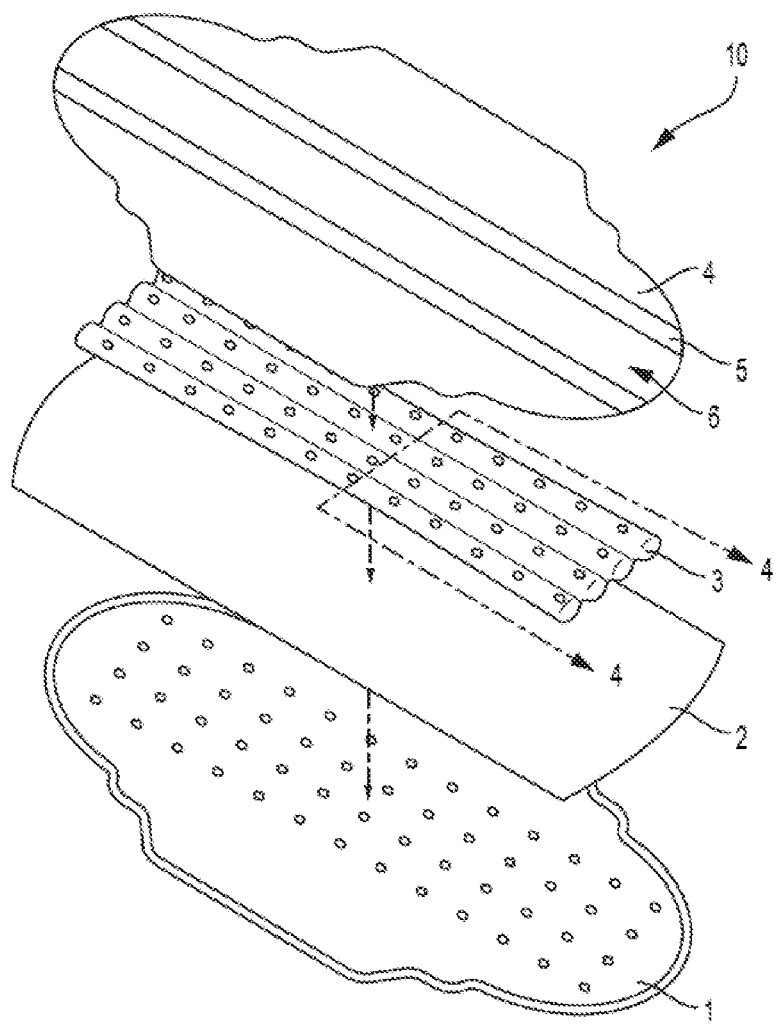
FIG. 3 is an exploded view of the absorbent pad from the backsheet downward showing an adhesive pattern to be applied to the back of the absorbent pad in accordance with an exemplary embodiment of the present invention.
Figure 4:
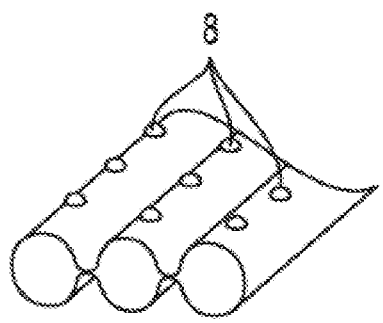
FIG. 4 is a cross-sectional view along line 4-4 of FIG. 3.

FIGS. 3 and 4 illustrate one exemplary manner of bonding absorbent core 3 to backsheet 4 along the flexure hinges 3b that enables absorbent core 3 to remain flexible even after bonding absorbent core 3 to backsheet 4. FIG. 3 shows an exploded view of absorbent pad 10 as viewed from the backsheet 4 downward. FIG. 4 shows a cross-sectional view of absorbent core 3 along line 4-4 of FIG. 3 and illustrates an exemplary pattern that can be used to bond absorbent pad 3 to backsheet 4.

In the exemplary embodiment shown in FIG. 3, a first pressure-sensitive adhesive 8 is applied at the bottom of the absorbent core 3, preferably only to the ridges 3a, to bond absorbent core 3 to backsheet 4. First adhesive 8 that is used to bond absorbent core 3 to backsheet 4 may be, for example, any type of hot melt adhesive. The absorbent core 3 is bonded to backsheet 4 with the first adhesive 8 in a first pattern that allows absorbent pad 10 to flex at flexure hinges 3b and recover from deformation even when wet and subject to lateral motion. In the embodiment shown in FIG. 3, the pattern of adhesive 8 is applied to each of ridges 3a of the absorbent core 3 as a row of droplets. In another exemplary embodiment shown in FIG. 5, the first adhesive 8' is applied as the pattern to each of the plurality of ridges 3a of the absorbent core 3 as a continuous filament of adhesive 8' connecting a plurality of spaced-apart spirals 12 of first adhesive 8. As an alternative, first adhesive 8 may be applied in other patterns or as adhesive strips along ridges 3a in which first adhesive 8 is only applied to ridges 3a and not to flexure hinges 3b such that first adhesive 8 does not spread to flexure hinges 3b and interfere with the flexibility of flexure hinges 3b. However, first adhesive 8 should be applied discontinuously across the width of the absorbent pad 10 to avoid application to the flexure hinges 3b.

A second adhesive 5 may also be applied to the bottom of backsheet 4 for removably attaching absorbent pad 10 to consumer underwear with an adhesive pattern that minimizes interference with the flexing of pad 10. Like first adhesive 8, second adhesive 5 may be any type of hot melt adhesive. For example, in one embodiment, second adhesive 5 is applied to the bottom of backsheet 4 as elongate adhesive strips that are sufficiently narrow so that they do not impede the flexing of the flexure hinges 3b. As is conventional in the art, the adhesive strips may be covered with a removable protective peel-off strip cover (not shown) that is removed before absorbent pad 10 is used and attached to consumer underwear.

Absorbent pad 10 is desirably thin so as to maintain a low profile. In an exemplary embodiment, absorbent pad 10 has a dry thickness (i.e., a thickness when it is dry) of at least 2 mm and no more than 10 mm, or more preferably a dry thickness of at least 2 mm and no more than 5 mm. Absorbent core 3 need not extend throughout the entire absorbent pad 10. Rather, absorbent core 3 may be confined to an absorbent center zone 9 of absorbent pad 10 that extends within the range of approximately 20% to 30%, or approximately 20% to 50%, of the surface area of the absorbent pad, generally at the center of the absorbent pad. For example, the absorbent center zone 9 may extend across 35 mm to 80 mm of the width of absorbent pad 10. The absorbent center zone 9 is shown in FIG. 1A.

To provide sufficient flexibility to absorbent pad 10, flexure hinges 3b may be spaced apart from one another along the width of absorbent pad 10, such as within a range of approximately 1/16 inch to 1/4 inch. In one embodiment, flexure hinges 3b are evenly spaced from one another. In other embodiments, flexure hinges 3b may be spaced apart from one another asymmetrically on a single absorbent pad 10.

An absorbent pad 10 made in accordance with an embodiment of the present invention can achieve an absorbent difference in flexural-resistance between the dry state and the wet state of the absorbent center zone 9 of less than 100 grams-force.

In an embodiment in which the absorbent core includes a foam, the foam that is used may be, for example, a resilient sheet of open-cell foam that has at least one of a polyether urethane foam, a polyester urethane foam, or a foam rubber, with SAP particles trapped in the foam. Where an absorbent core is comprised of a resilient sheet of an open-cell foam, the absorbent core need not be corrugated as the open-cell foam has flexible cell walls. An absorbent core made from resilient sheet of open-cell foam may have a durometer value in a range of between 25 to 55 IFD (indentation force deflection), or more preferably a durometer value in a range of between 35 to 40 IFD, and a density in a range of between 2.5 to 4 pcf (pounds per cubic foot) and more preferably a density of approximately 3 pcf.

In the present invention, topsheet 1 may be made of any suitable relatively liquid-permeable material currently known in the art or later discovered that permits passage of a liquid therethrough. Because topsheet 1 typically comes in contact with the skin of the wearer, it is preferably made of a material that is gentle to human skin. Examples of suitable topsheet materials include nonwoven, spun-bonded or carded webs of polypropylene, polyethylene, nylon, polyester and blends of these materials, or perforated, apertured or reticulated films, and the like. Nonwoven materials are exemplary because such materials readily allow the passage of liquids to the absorbent core 3, passing through liquid transfer layer 2, if present. Topsheet 1 is preferably formed of a single ply of nonwoven material that may be made of fibers comprising polypropylene, polyethylene, polyethylene terephthalate (PET), polylactide (PLA), nylon, polyester and blends of these materials which have been thermally bonded, spunbonded, spunlaced, hydroentangled, or a combination thereof, or a composite of nonwoven material, such as a spunbond-meltblown-spunbond (SMS) nonwoven. For example, the nonwoven material may have a basis weight of about 8-30 grams per square meter and have appropriate strength and softness for use as a topsheet in an application which will be in contact with human skin. Topsheet 1 may be treated with a surfactant, over the whole surface or a portion of the surface, rendering it hydrophilic to facilitate the passage of moisture through topsheet 1 and into the liquid transfer layer 2 and absorbent core 3.

Where present, liquid transfer layer 2 may be a single layer or multiple layers made of liquid-permeable synthetic or natural material, or a combination of both, or a single multilayer apertured film. Liquid transfer layer 2 serves to quickly collect and distribute discharged body fluid to absorbent core 3. Because such fluid is typically discharged in gushes, the area of absorbent core 3 proximate to the point of fluid discharge may be overwhelmed by its rate, resulting in a leak. The liquid transfer layer 2 facilitates transport of the fluid from the point of discharge across its surface area to contact other parts of absorbent core 3 from which it can be more readily absorbed. The use of a liquid transfer layer or ADL is well known in the art. Accordingly, liquid transfer layer 2 of the absorbent pad 10 may have any well known or as yet undiscovered construction.

Backsheet 70 may be made of a liquid-impermeable material or be comprised of multiple layers, in which one or more of the multiple layers serves as a liquid-impermeable barrier layer.

Figure 5A:
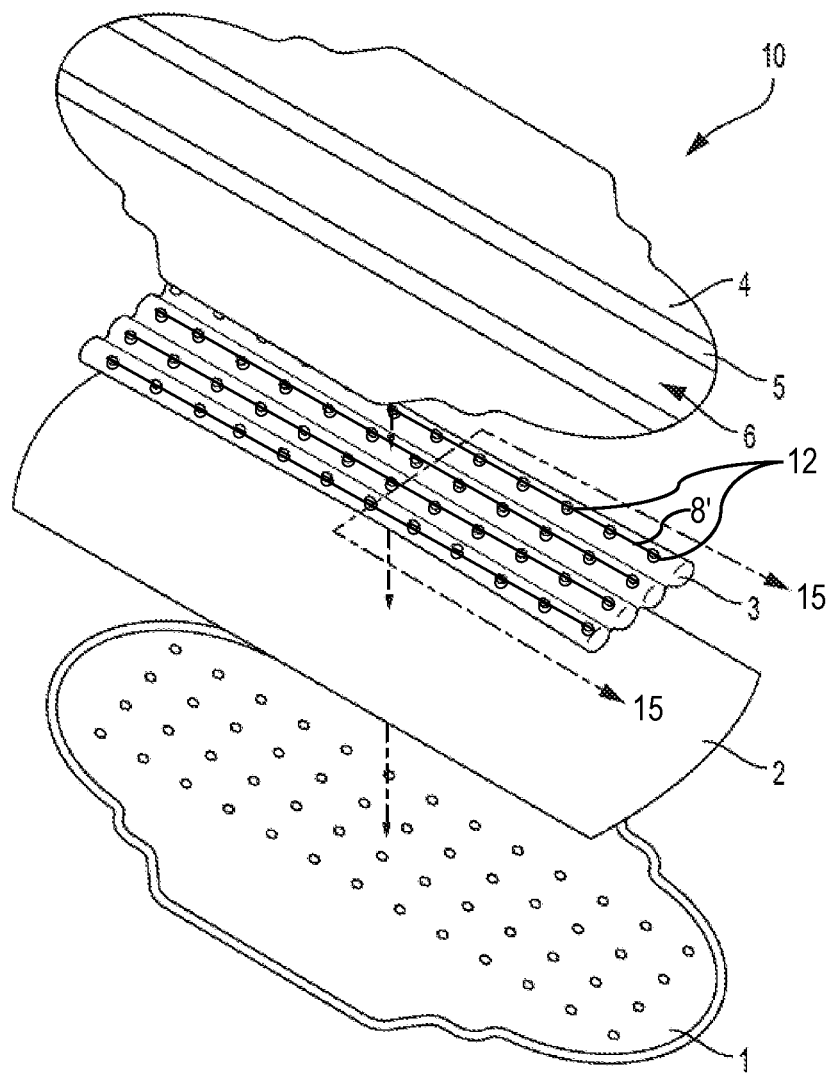
FIG. 5A is an exploded view of the absorbent pad from the backsheet downward showing an adhesive pattern to be applied to the back of the absorbent pad in accordance with an exemplary embodiment of the present invention.
Figure 5B:
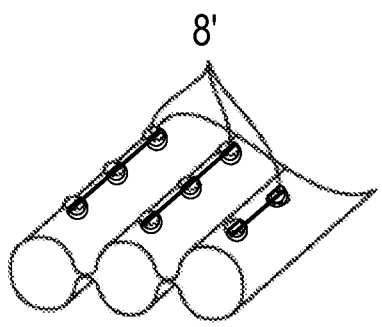
FIG. 5B is a cross-sectional view along line 15-15 of FIG. 5A.

In order to demonstrate the flexibility of an absorbent pad made in accordance with the present invention, the delta values between the dry and wet peak bending stiffness were measured for an absorbent pad with a corrugated laminate absorbent core with the adhesive pattern shown in FIG. 5A using a modified circular bend procedure, which is described in U.S. Pat. No. 4,950,264 (Osborn), which is incorporated herein by reference. Existing commercial products were similarly tested. The following is a description of the modified circular bend procedure that was used.

Modified Circular Bend Procedure

This procedure measures the flexural-resistance of a sanitary product, such as a sanitary napkin, by its peak bending stiffness. The peak bending stiffness is determined by a test modeled on the ASTM D 4032-82 CIRCULAR BEND PROCEDURE. The modified CIRCULAR BEND PROCEDURE provides a simultaneous multi-directional deformation of a material in which one face of a specimen becomes concave and the other face becomes convex. The procedure provides a result in the form of a force value related to flexural-resistance, which accounts for the simultaneous average stiffness in all directions.

The apparatus used for the CIRCULAR BEND PROCEDURE was a modified Circular Bend Stiffness Tester Flexure Resistance Jig for use in an Instron Tensile Tester Model #4411 or equivalent that tests for constant rate of travel. The jig has:

- a smooth-polished steel plate platform which is 102.0×102.0×6.35 millimeters having an 18.75 millimeter diameter orifice. The lap edge of the orifice is set at a 45 degree angle to a depth of 4.75 millimeters;
- a plunger having an overall length of 72.2 millimeters, a diameter of 6.25 millimeters, and a ball nose having a radius of 2.97 millimeters, the plunger being mounted concentric with the orifice and having equal clearance on all sides. The needle-point prevents lateral movement of the test specimen during testing. The bottom of the plunger should be set well above the top of the orifice plate. From this position, the downward stroke of the ball nose is to the exact bottom of the plate orifice.
- A force-measurement gauge and, more specifically, an Instron inverted compression load cell is used. The load cell has a load range of about 0.0 grams to about 2000.0 grams.
- An actuator, and more specifically the Instron Model No. 1122 having an inverted compression load cell is also used. The Instron 1122 is made by the Instron Engineering Corporation of Canton, Mass.

Number and Preparation of Specimens

In order to perform the procedure for this test, specimens are prepared from five product samples. Each specimen was 37.5×37.5 mm in size and cut from the center of each product. Each specimen included the full cross-section of the product (i.e., the backsheet, core and topsheet) and the layers were kept intact during the cutting process. The test specimens were not folded or bent, and the handling of specimens was kept to a minimum and to the edges to avoid affecting flexural-resistance properties.

Procedure

The specimens were conditioned by leaving them in a room which was 21+/−0.1° C. and 50+/−0.2% relative humidity for a period of two hours. The test plate was leveled and the plunger speed was set at 50.0 centimeters per minute per full stroke length. A specimen was centered on the orifice platform below the plunger such that the body facing surface of the specimens was facing the plunger and the garment facing surface of the specimen was facing the platform. The indicator zero was checked and adjusted, as necessary. The plunger was then actuated without the specimen being touched by the person performing the testing. The maximum force reading to the nearest gram was recorded as the peak binding stiffness value for the specimen. The above steps were repeated for five specimens of the product resulting in five peak binding stiffness values. The flexural resistance for the product was then calculated as the average of the five peak bending stiffness values.

The above test procedure provides the flexural resistance for a dry specimen of a product. For determining the wet flexural resistance, product specimens were created by imparting (e.g., pouring) 2 ml of saline into a dry product specimen and conducting the modified CIRCULAR BEND PROCEDURE approximately 60 sec after the liquid had been absorbed by the dry product specimen.

Example 1

Dry and wet specimens from sample absorbent pads made in accordance with an exemplary embodiment of the present invention were tested using the modified circular bend procedure. The sample absorbent pad included a corrugated laminate absorbent core with superabsorbent polymer (SAP) particles and flexure hinges. The absorbent core was 192 mm long and 43 mm wide and had 4.5 mm wide ridges extending the entire length of the absorbent core. The ridges were between 1.3 and 1.7 mm thick and the flexure hinges were approximately 0.5 mm thick.

Additional tests were also run on other commercial laminate absorbent products using this same modified circular bend procedure.

Figure 6:
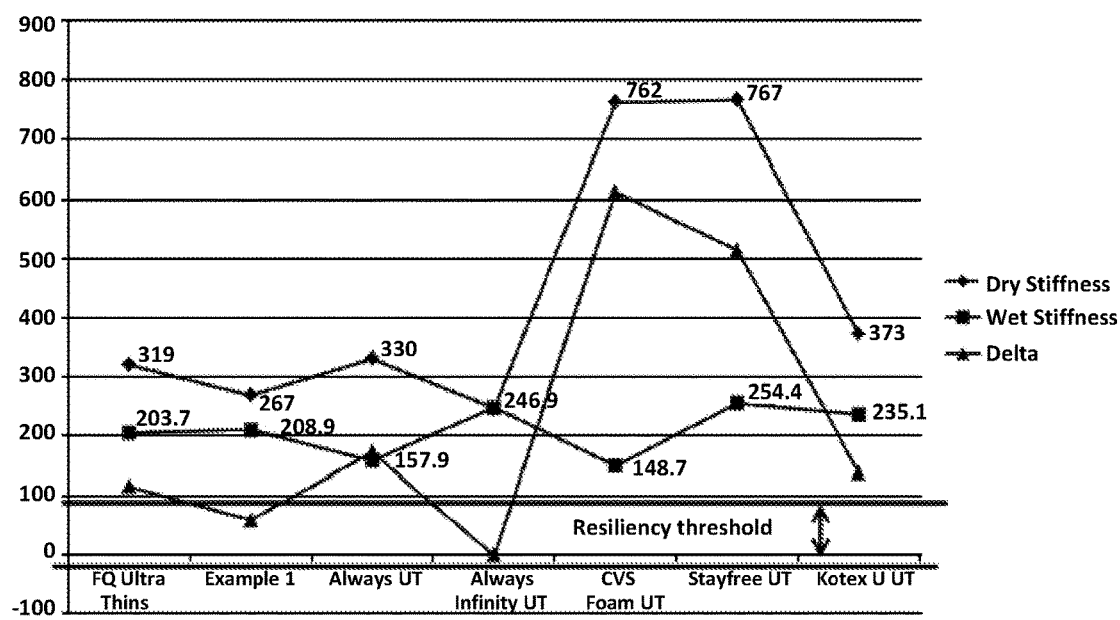
FIG. 6 is a graph that illustrates results of the flexural-resistance tests performed, using the modified circular bend procedure, on an absorbent pad made in accordance with exemplary embodiments of the present invention and on other commercial absorbent pads for comparison.

The test results for the various commercial laminate products and EXAMPLE 1 product were then compared. The results of the flexural-resistance tests using the modified circular bend procedure are set forth in Table 1 below and are plotted in FIG. 6 (where the vertical axis represents the peak bending stiffness in grams-force). In Table 1, the "dry stiffness" represents the average peak bending stiffness in grams-force of the tested dry product specimens and the "wet stiffness" represents the average peak bending stiffness in grams-force of the wet product specimens, which correspond to the dry product specimens after liquid has been imparted to them. The difference or "delta" in flexural-resistance between the dry state and the wet state of the absorbent products that were tested is shown in FIG. 6. It is desired to maintain the delta value below the "resiliency threshold" of 100 grams-force to maintain the flexibility of a flexible absorbent pad.

TABLE 1

|  | Dry Stiffness (gf) | Wet Stiffness (gf) | Delta - FIG. 6 (gf) |
| --- | --- | --- | --- |
| EXAMPLE 1 | 267 | 209 | 59 |
| First Quality ® Ultra Thins | 319 | 204 | 116 |
| Always ® UT | 330 | 158 | 172 |
| Always ® Infinity ® UT | 245 | 247 | −2 |
| CVS Foam UT | 762 | 149 | 613 |
| Stayfree ® UT | 767 | 254 | 513 |
| Kotex ® U UT | 373 | 235 | 138 |

The data collected suggests that only the superabsorbent pads made according to the present invention (labeled "EXAMPLE 1") that each contain a flexible corrugated laminate absorbent core with SAP particles and flexure hinges delivered a flexible delta between dry and wet stiffness that was below 100 gf. The results for the present invention compared very well to the test results for the Always® Infinity® pad from P&G, which is not a superabsorbent pad, but is rather a high internal phase emulsion polyethylene foam absorbent pad that uses a water-based emulsion that does not contain SAP particles, but has a desirably small delta between dry and wet stiffness. The consequence of a small delta is that an absorbent pad in accordance with the present invention remains comfortable even when wet.

While this invention has been described in conjunction with the exemplary embodiments outlined above, it is evident that many alternatives, modifications and variations will be apparent to those skilled in the art. Accordingly, the exemplary embodiments of the invention, as set forth above, are intended to be illustrative, not limiting. Various changes may be made without departing from the spirit and scope of the invention.

What is claimed is:

1. An absorbent pad comprising:
a liquid permeable topsheet;
an absorbent core disposed below the topsheet and comprising superabsorbent polymer particles and having a plurality of ridges of a first thickness separated by one or more flexure hinges of a second thickness less than the first thickness to permit flexing of the absorbent core about the one or more flexure hinges, the absorbent core having an entire length that extends from a first longitudinal end and a second longitudinal end of the absorbent core, both the ridges and the flexure hinges extending lengthwise across the entire length of the absorbent core in a continuous manner with the ridges interleaved with the one or more flexure hinges; and
a backsheet disposed below the absorbent core and comprising a liquid impermeable layer;
wherein the absorbent core is bonded to the backsheet with a first adhesive that is applied as a pattern of adhesive to at least one of the plurality of ridges on the absorbent core before the backsheet is bonded to the absorbent core, and the pattern of adhesive is not applied to the one or more flexure hinges, to keep the one or more flexure hinges substantially devoid of adhesive.

2. The absorbent pad of claim 1, wherein the absorbent pad has a dry thickness of between 2 mm and 10 mm.

3. The absorbent pad of claim 2, wherein a first section of the absorbent pad extends within an absorbent center zone of the absorbent pad.

4. The absorbent pad of claim 3, wherein the absorbent center zone extends within the absorbent pad across approximately 20%-50% of the surface area of the absorbent pad.

5. The absorbent pad of claim 1, wherein the absorbent core is corrugated.

6. The absorbent pad of claim 1, wherein the difference in flexural-resistance between the dry state and the wet state of the absorbent pad is less than 100 grams-force.

7. The absorbent pad of claim 1, further comprising a liquid transfer layer between the absorbent core and the liquid permeable topsheet.

8. The absorbent pad of claim 1, wherein the absorbent core comprises an airlaid material.

9. The absorbent pad of claim 1, wherein the absorbent core comprises a foam.

10. The absorbent pad of claim 1, wherein the absorbent core comprises one of a carded polyethylene terephthalate (PET) or a mixture of PET and polypropylene (PP) blended in one of a through-air fabric or a resin bonded fabric.

11. An absorbent pad comprising:
a liquid permeable topsheet;
an absorbent core disposed below the topsheet and comprising superabsorbent polymer particles and having a plurality of ridges separated by one or more flexure hinges, the absorbent core having an entire length that extends from a first longitudinal end and a second longitudinal end of the absorbent core, both the ridges and the flexure hinges extending lengthwise across the entire length of the absorbent core in a continuous manner with the ridges interleaved with the one or more flexure hinges; and
a backsheet disposed below the absorbent core and comprising a liquid impermeable layer;
wherein the absorbent pad has a dry thickness of between 2 mm and 10 mm;
wherein the difference in flexural-resistance between the dry state and the wet state of the absorbent pad is less than 100 grams-force; and
wherein the absorbent core is bonded to the backsheet with a first adhesive that is applied as a pattern of adhesive to at least one of the plurality of ridges on the absorbent core before the backsheet is bonded to the absorbent core, and the pattern of adhesive is not applied to the one or more flexure hinges, to keep the one or more flexure hinges substantially devoid of adhesive.

12. The absorbent pad of claim 11, wherein the absorbent pad comprises an absorbent center zone that extends within the absorbent pad across approximately 20%-50% of the surface area of the absorbent pad.

13. The absorbent pad of claim 11, wherein the absorbent core is corrugated.

14. The absorbent pad of claim 11, wherein the absorbent core comprises an airlaid material.

15. The absorbent pad of claim 11, wherein the absorbent core comprises a foam.

16. The absorbent pad of claim 11, further comprising a liquid transfer layer between the absorbent core and the liquid permeable topsheet.

17. The absorbent pad of claim 11, wherein the absorbent core comprises one of a carded polyethylene terephthalate (PET) or a mixture of PET and polypropylene (PP) blended in one of a through-air fabric or a resin bonded fabric.

* * * * *